(12) United States Patent
Bateman et al.

(10) Patent No.: US 9,520,279 B2
(45) Date of Patent: *Dec. 13, 2016

(54) MASS SPECTROMETER

(71) Applicant: Micromass UK Limited, Wilmslow (GB)

(72) Inventors: Robert Harold Bateman, Cheshire (GB); Kevin Giles, Cheshire (GB); Steven Derek Pringle, Darwen (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 19 days.

This patent is subject to a terminal disclaimer.

(21) Appl. No.: 14/617,050

(22) Filed: Feb. 9, 2015

(65) Prior Publication Data
US 2015/0155150 A1 Jun. 4, 2015

Related U.S. Application Data

(63) Continuation of application No. 12/092,601, filed as application No. PCT/GB2006/004202 on Nov. 10, 2006, now Pat. No. 8,952,323.

(60) Provisional application No. 60/737,150, filed on Nov. 16, 2005.

(30) Foreign Application Priority Data

Nov. 10, 2005 (GB) .................................. 0522933.1

(51) Int. Cl.
*H01J 49/00* (2006.01)
*H01J 49/06* (2006.01)
*G01N 27/62* (2006.01)

(52) U.S. Cl.
CPC .......... *H01J 49/062* (2013.01); *G01N 27/622* (2013.01); *H01J 49/0031* (2013.01); *H01J 49/0045* (2013.01)

(58) Field of Classification Search
USPC ........................ 250/281, 282, 283, 290, 293
See application file for complete search history.

(56) References Cited

U.S. PATENT DOCUMENTS

| | | | |
|---|---|---|---|
| 4,855,595 | A | 8/1989 | Blanchard |
| 6,621,077 | B1 | 9/2003 | Guevremont et al. |
| 6,791,078 | B2 | 9/2004 | Giles et al. |
| 6,872,939 | B2 | 3/2005 | Bateman et al. |
| 6,884,995 | B2 | 4/2005 | Bateman et al. |
| 6,906,319 | B2 | 6/2005 | Hoyes |
| 6,914,241 | B2 | 7/2005 | Giles et al. |
| 6,992,283 | B2 | 1/2006 | Bateman et al. |
| 7,071,467 | B2 | 7/2006 | Bateman et al. |

(Continued)

*Primary Examiner* — Nicole Ippolito
*Assistant Examiner* — Hanway Chang
(74) *Attorney, Agent, or Firm* — Diederiks & Whitelaw, PLC

(57) ABSTRACT

A mass spectrometer is disclosed comprising a first ion trap or ion guide, a single ion mobility spectrometer or separator stage and a second ion trap or ion guide arranged downstream of the ion mobility spectrometer or separator. A mode of operation includes passing ions from said first ion trap or ion guide to said device and onwards to said second ion trap or ion guide and then passing at least some of said ions or at least some fragment, daughter, product or adduct ions derived from said ions from said second ion trap or ion guide onwards to said first ion trap or ion guide.

21 Claims, 7 Drawing Sheets

(56) References Cited

U.S. PATENT DOCUMENTS

| | | |
|---|---|---|
| 7,728,288 B2 | 6/2010 | Makarov et al. |
| 8,952,323 B2 * | 2/2015 | Bateman et al. ............. 250/282 |
| 2003/0213900 A1 | 11/2003 | Hoyes |
| 2004/0031920 A1 | 2/2004 | Giles et al. |

* cited by examiner

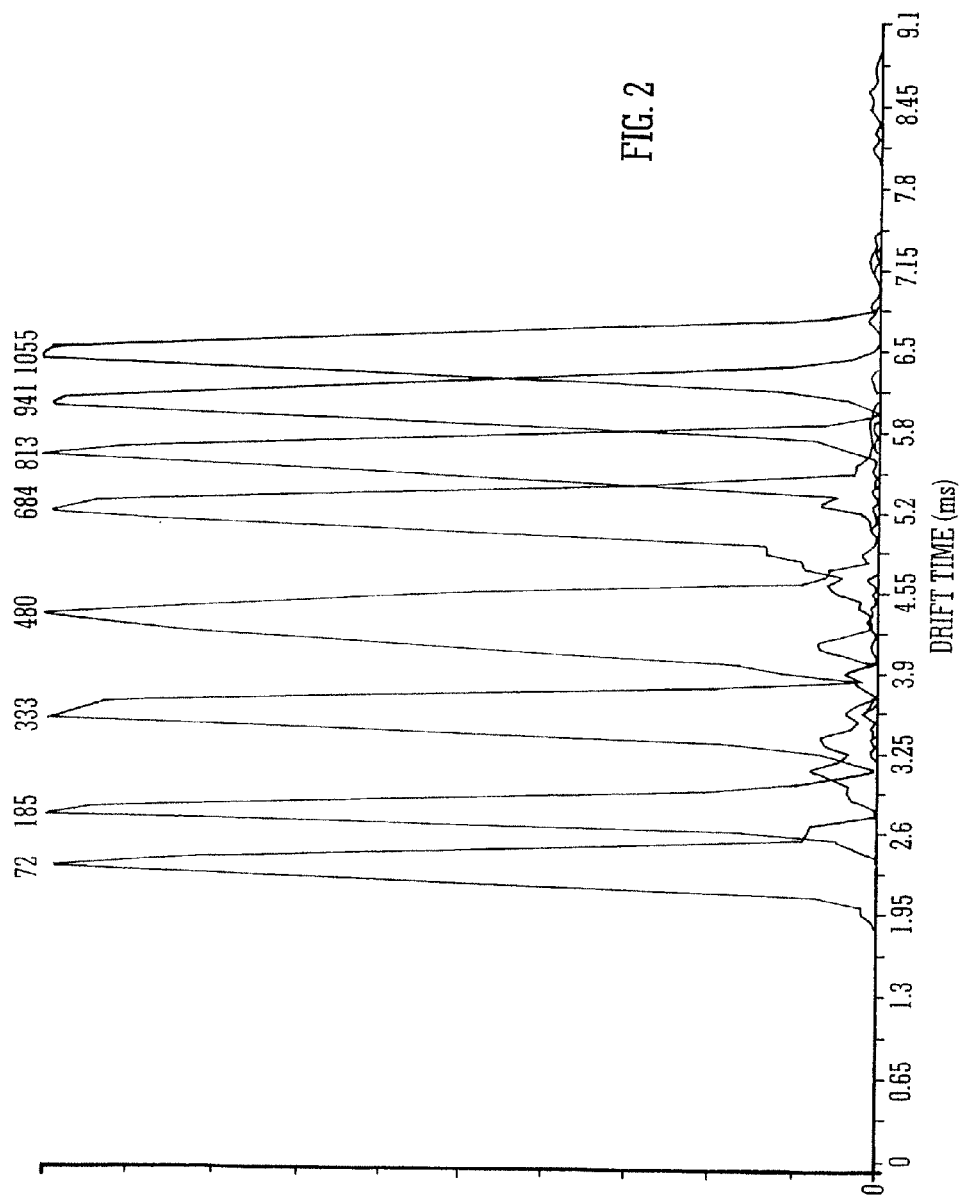

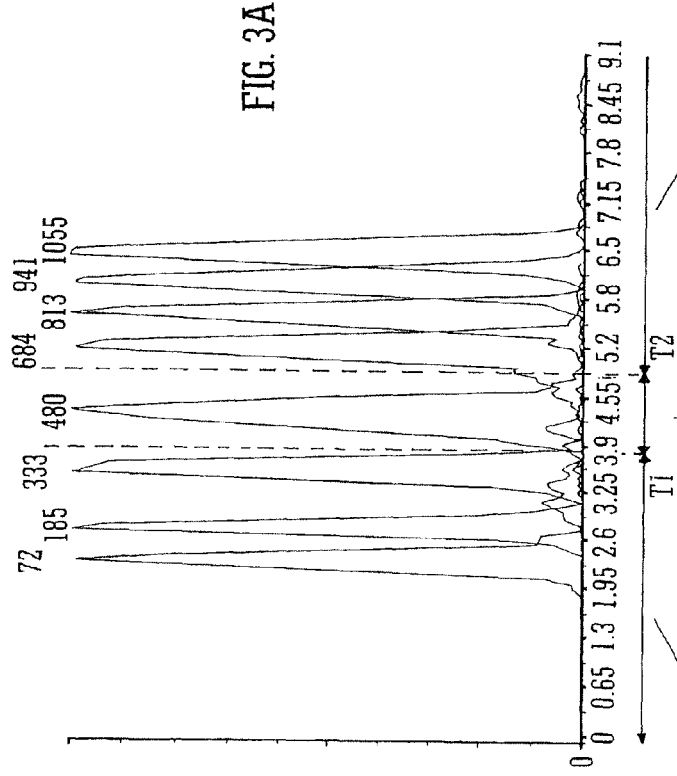
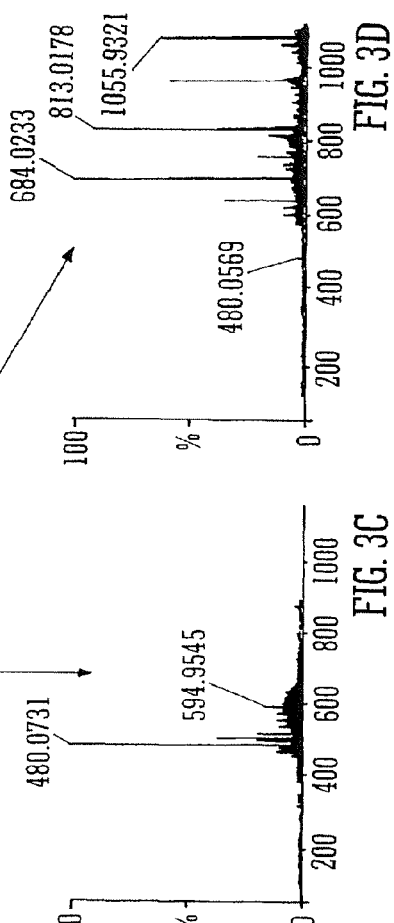

FIG. 4

MASS SPECTROMETER

CROSS-REFERENCE TO RELATED APPLICATION

This application is a continuation of U.S. patent application Ser. No. 12/092,601 filed on Aug. 20, 2008 which represents a National Stage of International Application No. PCT/GB2006/004202 filed on Nov. 10, 2006 and claims the benefit of U.S. Provisional Patent Application Ser. No. 60/737,150 filed on Nov. 16, 2005 and United Kingdom Application No. 0522933.1 filed on Nov. 10, 2005. The entire contents of these applications are incorporated by reference.

BACKGROUND OF THE INVENTION

The present invention relates to a mass spectrometer and a method of mass spectrometry.

Mass spectrometry is an established technique for identifying and quantifying molecules, including molecules of biological interest. It is a primary technique for identifying proteins due to its unparalleled speed, sensitivity and specificity. Strategies for the analysis of proteins may involve either analysis of the intact protein or more commonly digestion of the protein using a specific protease that cleaves at predictable residues along the peptide backbone. This provides smaller stretches of peptide sequence that are more amenable to analysis via mass spectrometry.

It is known to perform experiments which involve the separation of a complex digest mixture by liquid chromatography which is directly interfaced to a tandem mass spectrometer using Electrospray Ionisation (ESI). MS and MS/MS spectra may be collected throughout the chromatographic separation and this information may be used to search databases directly for matching sequences leading to identification of the parent protein.

The known approach can be used to identify proteins that are present at low endogenous concentrations. However, such digest mixtures may contain many hundreds if not thousands of components many of which will co-elute from the chromatography column. Methods designed for analysis of digest mixtures aim to identify as many of the peaks as possible within the complex mixture. However, as sample complexity increases it becomes increasingly difficult to select each individual precursor or parent ion for subsequent fragmentation.

One method of increasing the peak capacity is to fragment a large number of parent or precursor ions simultaneously and then to record their product or fragment ions. Product or fragment ions may be associated with parent or precursor ions according to the closeness of alignment of their LC elution times. Eventually, however, as the sample complexity increases this method may also fail.

Another approach to the problem of highly complex mixtures is to improve the separation capability. Addition of a further orthogonal separation stage can be particularly effective, especially if the time requirements for each separation process and for the mass spectrometer do not overlap.

One known method which may be used to separate ions prior to analysis by mass spectrometry is that of ion mobility spectrometry or gas phase electrophoresis. One form of an ion mobility spectrometer or separator comprises a drift tube or cell wherein an axial electric field is maintained in the presence of a buffer gas. Higher mobility ions pass more quickly along the length of the ion mobility spectrometer or separator than lower mobility ions. As a result ions are separated according to their ion mobility.

A known ion mobility spectrometer or separator may operate at or around atmospheric pressure or under a partial vacuum at a pressure down to as low as about 0.01 mbar. The known ion mobility spectrometer or separator operating under a partial vacuum comprises a plurality of electrodes having apertures. A DC voltage gradient is maintained along the length of the ion mobility spectrometer or separator and the electrodes are connected to an AC or RF voltage supply. This form of ion mobility spectrometer or separator is advantageous in that the AC or RF voltage which is applied to the electrodes results in radial confinement of the ions passing through the ion mobility spectrometer or separator. Radial confinement of the ions results in higher ion transmission compared with an ion mobility spectrometer or separator which does not confine ions radially.

An ion mobility spectrometer or separator is known wherein ions are confined radially by an inhomogeneous RF field in an ion guide and ions are propelled forward by a potential hill or barrier that is progressively applied along the axis of the ion guide in the presence of a buffer gas. Appropriate selection of the amplitude and velocity of the potential hill or barrier which is translated along the length of the ion guide and the type and pressure of gas allows ions to slip selectively over the potential hill or barrier according to their ion mobility. This in turn allows ions having different ion mobilities to be transported at different velocities along the ion guide and thereby to become temporally separated.

The additional separation gained by the use of ion mobility separation (IMS) or gas phase electrophoresis increases the peak capacity of a mass spectrometer. This benefit is gained irrespective of whether or not other separation techniques such as Liquid Chromatography (LC) are also used. Furthermore, the benefit gained by the use of ion mobility separation is equally relevant to tandem mass spectrometers (MS/MS) in which parent ions may be mass analysed and then selected parent ions may be induced to fragment by Collision Induced Decomposition and wherein the resulting fragment or daughter ions are then mass analysed.

It is desired to provide a mass spectrometer having an improved ability to separate ions according to their ion mobility.

SUMMARY OF THE INVENTION

According to an aspect of the present invention there is provided a mass spectrometer comprising:
a first ion trap or ion guide comprising a plurality of electrodes;
a device for separating ions according to their ion mobility or rate of change of ion mobility with electric field strength, the device being arranged downstream of the first ion trap or ion guide; and
a second ion trap or ion guide comprising a plurality of electrodes arranged downstream of the device, wherein the second ion trap or ion guide is arranged and adapted in a mode of operation to pass or transmit ions from the second ion trap or ion guide to the device.

According to the preferred embodiment the first ion trap or ion guide is preferably arranged and adapted in a mode of operation to receive ions which emerge from the device. The first ion trap or ion guide is preferably arranged and adapted in a mode of operation to receive ions which emerge from the device and to pass or transmit at least some of the ions, or at least some fragment, daughter, product or adduct ions derived from the ions, from the first ion trap or ion guide to the device.

The first ion trap or ion guide may comprise a multipole rod set or a segmented multipole rod set ion trap or ion guide comprising a quadrupole rod set, a hexapole rod set, an octapole rod set or a rod set comprising more than eight rods. Alternatively, the first ion trap or ion guide may comprise an ion tunnel or ion funnel ion trap or ion guide comprising a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. According to another embodiment the first ion trap or ion guide may comprise a stack or array of planar, plate or mesh electrodes, wherein the stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes and wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. According to another embodiment the first ion trap or ion guide may comprise an ion trap or ion guide comprising a plurality of groups of electrodes arranged axially along the length of the ion trap or ion guide, wherein each group of electrodes comprises: (a) a first and a second electrode and means for applying a DC voltage or potential to the first and second electrodes in order to confine ions in a first radial direction within the ion guide; and (b) a third and a fourth electrode and means for applying an AC or RF voltage to the third and fourth electrodes in order to confine ions in a second radial direction within the ion guide. The second radial direction is preferably orthogonal to the first radial direction.

According to the preferred embodiment the first ion trap or ion guide comprises an ion tunnel or ion funnel ion trap or ion guide wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The first ion trap or ion guide preferably further comprises first AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the first ion trap or ion guide in order to confine ions radially within the first ion trap or ion guide. The first AC or RF voltage means is preferably arranged and adapted to apply an AC or RF voltage having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The first AC or RF voltage means is preferably arranged and adapted to apply an AC or RF voltage having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The first ion trap or ion guide is preferably arranged and adapted to receive a beam or group of ions and to convert or partition the beam or group of ions such that a plurality or at least 1, 2, 3, 4, 5, 6, 7, 8, 9, 10, 11, 12, 13, 14, 15, 16, 17, 18, 19 or 20 separate packets of ions are confined and/or isolated in the first ion trap or ion guide at any particular time. Each packet of ions is preferably separately confined and/or isolated in a separate real axial potential well formed within the first ion trap or ion guide.

The mass spectrometer preferably further comprises means arranged and adapted to urge at least some ions upstream and/or downstream through or along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion trap or ion guide in a mode of operation.

According to the preferred embodiment first transient DC voltage means are provided which are arranged and adapted to apply one or more transient DC voltages or potentials or one or more transient DC voltage or potential waveforms to the electrodes forming the first ion trap or ion guide in order to urge at least some ions upstream and/or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion trap or ion guide.

According to a less preferred embodiment AC or RF voltage means may be provided and may be arranged and adapted to apply two or more phase-shifted AC or RF voltages to electrodes forming the first ion trap or ion guide in order to urge at least some ions upstream and/or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion trap or ion guide.

The mass spectrometer preferably comprises means arranged and adapted in a mode of operation to maintain at least a portion of the first ion trap or ion guide at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >1 mbar; (viii) 0.0001-100 mbar; and (ix) 0.001-10 mbar.

According to an embodiment first acceleration means are preferably provided which are arranged and adapted to accelerate ions into the first ion trap or ion guide wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment or react upon entering the first ion trap or ion guide. The first acceleration means preferably accelerates ions from the ion mobility spectrometer or separator into the first ion trap or ion guide.

A control system is preferably arranged and adapted to switch or repeatedly switch the potential difference through which ions pass prior to entering the first ion trap or ion guide between a relatively high fragmentation or reaction mode of operation wherein ions are substantially fragmented or reacted upon entering the first ion trap or ion guide and a relatively low fragmentation or reaction mode of operation wherein substantially fewer ions are fragmented or reacted or wherein substantially no ions are fragmented or reacted upon entering the first ion trap or ion guide. In the relatively high fragmentation or reaction mode of operation ions entering the first ion trap or ion guide are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; (x) ≥100 V; (xi) ≥110 V; (xii) ≥120 V; (xiii) ≥130 V; (xiv) ≥140 V; (xv) ≥150 V; (xvi) ≥160 V; (xvii) ≥170 V; (xviii) ≥180 V; (xix) ≥190 V; and (xx) ≥200 V. In the relatively low fragmentation or reaction mode of operation ions entering the first ion trap or ion guide are preferably accelerated through a potential difference selected from the group consisting of: (i) ≤20 V; (ii) ≤15 V; (iii) ≤10 V; (iv) ≤5V; and (v) ≤1V.

The device which is preferably arranged downstream of the first ion trap or ion guide preferably comprises an ion mobility spectrometer or separator which is preferably arranged to separate ions according to their ion mobility. The device preferably comprises a gas phase electrophoresis device.

The ion mobility spectrometer or separator is preferably arranged to temporally separate ions according to their ion mobility which emerge from or which have been transmitted or received from the first ion trap or ion guide and/or the second ion trap or guide.

The ion mobility spectrometer or separator may comprise either: (i) a drift tube comprising one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube; (ii) a multipole rod set or a segmented multipole rod set comprising a quadrupole rod set, a hexapole rod set, an octapole rod set or a rod set comprising more than eight rods; (iii) an ion tunnel or ion funnel comprising a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area; (iv) a stack or array of planar, plate or mesh electrodes, wherein the stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use; or (v) a plurality of groups of electrodes arranged axially along the length of the ion trap or ion guide, wherein each group of electrodes comprises: (a) a first and a second electrode and means for applying a DC voltage or potential to the first and second electrodes in order to confine ions in a first radial direction within the device; and (b) a third and a fourth electrode and means for applying an AC or RF voltage to the third and fourth electrodes in order to confine ions in a second radial direction (which is preferably orthogonal to the first radial direction) within the device.

According to the preferred embodiment the ion mobility spectrometer or separator preferably comprises an ion tunnel or ion funnel wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The ion mobility spectrometer or separator preferably further comprises a second AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the ion mobility spectrometer or separator in order to confine ions radially within the ion mobility spectrometer or separator. The second AC or RF voltage means is preferably arranged and adapted to apply an AC or RF voltage having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The second AC or RF voltage means is preferably arranged and adapted to apply an AC or RF voltage having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to the preferred embodiment the ion mobility spectrometer or separator preferably comprises second transient DC voltage means arranged and adapted to apply one or more transient DC voltages or potentials or one or more transient DC voltage or potential waveforms to electrodes forming the ion mobility spectrometer or separator in order to urge at least some ions upstream and/or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to a less preferred embodiment the ion mobility spectrometer or separator may comprise AC or RF voltage means arranged and adapted to apply two or more phase-shifted AC or RF voltages to electrodes forming the ion mobility spectrometer or separator in order to urge at least some ions upstream and/or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The mass spectrometer preferably comprises means arranged and adapted in a mode of operation to maintain at least a portion or substantially the whole of the ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) 0.001-100 mbar; (viii) 0.01-10 mbar; and (ix) 0.1-1 mbar.

According to a less preferred embodiment the device arranged downstream of the first ion trap or ion guide may comprise a Field Asymmetric Ion Mobility Spectrometer ("FAIMS") device which is arranged to separate ions according to their rate of change of ion mobility with electric field strength. The Field Asymmetric Ion Mobility Spectrometer device may comprise at least a first electrode and a second electrode. Ions may be arranged to be received, in use, between the first and second electrodes. According to an embodiment the FAIMS device may further comprise means for applying: (i) an asymmetric periodic voltage waveform to the first and/or second electrodes, wherein the asymmetric periodic voltage waveform has a peak positive voltage and a peak negative voltage; and (ii) a DC compensation voltage to the first and/or second electrodes, wherein the DC compensation voltage preferably acts to counterbalance or counteract a force which would otherwise cause desired ions to drift towards the first and/or second electrodes.

According to an embodiment the second ion trap or ion guide may comprise either: (i) a multipole rod set or a segmented multipole rod set comprising a quadrupole rod set, a hexapole rod set, an octapole rod set or a rod set comprising more than eight rods; (ii) an ion tunnel or ion funnel comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area; (iii) a stack or array of planar, plate or mesh electrodes, wherein the stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use; or (iv) an ion trap or ion guide comprising a plurality of groups of electrodes arranged axially along the length of the ion trap or ion guide, wherein each group of electrodes comprises: (a) a first and a second electrode and means for applying a DC voltage or potential to the first and second electrodes in order to confine ions in a first radial direction within the ion guide; and (b) a third and a fourth electrode and means for applying an AC or RF voltage to the third and fourth electrodes in order to confine ions in a second radial direction (which is preferably orthogonal to the first radial direction) within the ion guide.

According to an embodiment the second ion trap or ion guide preferably comprises an ion tunnel or ion funnel wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The second ion trap or ion guide may further comprise third AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the second ion trap or ion guide in order to confine ions radially within the second ion trap or ion guide. The third AC or RF voltage means is preferably arranged and adapted to apply an AC or RF voltage having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The third AC or RF voltage means is preferably arranged and adapted to apply an AC or RF voltage having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The second ion trap or ion guide is preferably arranged and adapted to receive a beam or group of ions and to convert or partition the beam or group of ions such that a plurality or at least 1, 2, 3, 4, 5, 6, 7, 8, 9, 10, 11, 12, 13, 14, 15, 16, 17, 18, 19 or 20 separate packets of ions are confined and/or isolated in the second ion trap or ion guide at any particular time. Each packet of ions is preferably separately confined and/or isolated in a separate real axial potential well formed within the second ion trap or ion guide.

According to an embodiment the mass spectrometer preferably comprises means arranged and adapted to urge at least some ions upstream and/or downstream through or along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion trap or ion guide in a mode of operation.

According to an embodiment the mass spectrometer further comprises third transient DC voltage means arranged and adapted to apply one or more transient DC voltages or potentials or one or more transient DC voltage or potential waveforms to the electrodes forming the second ion trap or ion guide in order to urge at least some ions upstream and/or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion trap or ion guide.

According to a less preferred embodiment the mass spectrometer may further comprise AC or RF voltage means arranged and adapted to apply two or more phase-shifted AC or RF voltages to electrodes forming the second ion trap or ion guide in order to urge at least some ions upstream and/or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion trap or ion guide.

The mass spectrometer preferably further comprises means arranged and adapted in a mode of operation to maintain at least a portion of the second ion trap or ion guide at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >1 mbar; (viii) 0.0001-100 mbar; and (ix) 0.001-10 mbar.

According to an embodiment the mass spectrometer preferably further comprises second acceleration means arranged and adapted to accelerate ions into the second ion trap or ion guide wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment or react upon entering the second ion trap or ion guide.

The second acceleration means preferably accelerates ions from the ion mobility spectrometer or separator into the second ion trap or ion guide.

The mass spectrometer preferably comprises a control system arranged and adapted to switch or repeatedly switch the potential difference through which ions pass prior to entering the second ion trap or ion guide between a relatively high fragmentation or reaction mode of operation wherein ions are substantially fragmented or reacted upon entering the second ion trap or ion guide and a relatively low fragmentation or reaction mode of operation wherein substantially fewer ions are fragmented or reacted or wherein substantially no ions are fragmented or reacted upon entering the second ion trap or ion guide. In the relatively high fragmentation or reaction mode of operation ions entering the second ion trap or ion guide are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; (x) ≥100 V; (xi) ≥110 V; (xii) ≥120 V; (xiii) ≥130 V; (xiv) ≥140 V; (xv) ≥150 V; (xvi) ≥160 V; (xvii) ≥170 V; (xviii) ≥180 V; (xix) ≥190 V; and (xx) ≥200 V. In the relatively low fragmentation or reaction mode of operation ions entering the second ion trap or ion guide are preferably accelerated through a potential difference selected from the group consisting of: (i) ≤20 V; (ii) ≤15 V; (iii) ≤10 V; (iv) ≤5V; and (v) ≤1V.

According to an embodiment the mass spectrometer preferably further comprises an ion gate or deflection system arranged upstream and/or downstream of the device arranged downstream of the first ion trap or ion guide. The ion gate or deflection system preferably attenuates ions exiting the device which have an undesired transit time through the device or an undesired ion mobility, mass to charge ratio or rate of change of ion mobility with electric field strength.

A first mass filter or mass analyser may be arranged upstream and/or downstream of the first ion trap or ion guide. The first mass filter or mass analyser is preferably selected from the group consisting of: (i) a quadrupole rod set mass filter or mass analyser; (ii) a Time of Flight mass filter or mass analyser; (iii) a Wein filter; and (iv) a magnetic sector mass filter or mass analyser. In a mode of operation the first mass filter or mass analyser may be operated in a substantially non-resolving or ion guiding mode of operation. In another mode of operation the first mass filter or mass analyser may be scanned or a mass to charge ratio transmission window of the first mass filter or mass analyser may be varied with time.

A second mass filter or mass analyser may be arranged upstream and/or downstream of the second ion trap or ion guide. The second mass filter or mass analyser is preferably selected from the group consisting of: (i) a quadrupole rod set mass filter or mass analyser; (ii) a Time of Flight mass filter or mass analyser; (iii) a Wein filter; and (iv) a magnetic sector mass filter or analyser. In a mode of operation the second mass filter or mass analyser may be operated in a substantially non-resolving or ion guiding mode of operation. In another mode of operation the second mass filter or mass analyser is preferably scanned or a mass to charge ratio transmission window of the second mass filter or mass analyser is preferably varied with time.

According to an embodiment in a mode of operation the first mass filter or mass analyser and/or the second mass filter or mass analyser may be scanned or a mass to charge ratio transmission window of the first mass filter or mass analyser and/or the second mass filter or mass analyser may be varied with time preferably in synchronism with the operation of the device or the ion mobility or rate of change of ion mobility with electric field strength of ions emerging from and/or being transmitted to the device.

According to an embodiment in a mode of operation the first mass filter or mass analyser is preferably scanned or a mass to charge ratio transmission window of the first mass filter or mass analyser is preferably varied with time in synchronism with the operation of the second mass filter or mass analyser.

The mass spectrometer may comprise a collision, fragmentation or reaction device arranged and adapted to fragment ions by Collision Induced Dissociation ("CID").

According to a less preferred embodiment the mass spectrometer may comprise a collision, fragmentation or reaction device selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

According to an embodiment the collision, fragmentation or reaction device preferably forms at least part of the first ion trap or ion guide and/or the device and/or the second ion trap or ion guide. According to an alternative embodiment the collision, fragmentation or reaction device may be arranged upstream and/or downstream of the first ion trap or ion guide and/or the device and/or the second ion trap or ion guide.

The mass spectrometer preferably comprises an ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation On Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ("AP-MALDI") ion source; and (xviii) a Thermospray ion source.

The ion source may comprise a pulsed or continuous ion source.

The mass spectrometer preferably further comprises separation means for separating molecules from a mixture of other molecules prior to being ionised. The separation means is preferably selected from the group consisting of: (i) High Performance Liquid Chromatography ("HPLC"); (ii) anion exchange; (iii) anion exchange chromatography; (iv) cation exchange; (v) cation exchange chromatography; (vi) ion pair reversed-phase chromatography; (vii) chromatography; (vii) single dimensional electrophoresis; (ix) multi-dimensional electrophoresis; (x) size exclusion; (xi) affinity; (xii) reverse phase chromatography; (xiii) Capillary Electrophoresis Chromatography ("CEC"); (xiv) electrophoresis; (xv) ion mobility separation; (xvi) Field Asymmetric Ion Mobility Separation ("FAIMS"); and (xvi) capillary electrophoresis.

According to an embodiment the ion source is provided with an eluent over a period of time. The eluent is preferably separated from a mixture by means of liquid chromatography or capillary electrophoresis. According to a less preferred embodiment the ion source may be provided with an eluent over a period of time wherein the eluent has been separated from a mixture by means of gas chromatography.

The mass spectrometer preferably further comprises a mass analyser. The mass analyser is preferably arranged downstream of the second ion trap or ion guide. The mass analyser is preferably selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; (xiv) an axial acceleration Time of Flight mass analyser; and (xv) a quadrupole rod set mass filter or mass analyser.

According to an aspect of the present invention there is provided a method of mass spectrometry comprising:
providing a first ion trap or ion guide;
separating ions according to their ion mobility or rate of change of ion mobility with electric field strength in a device, the device being arranged downstream of the first ion trap or ion guide;
providing a second ion trap or ion guide arranged downstream of the device; and
passing or transmitting ions from the second ion trap or ion guide to the device.

According to an aspect of the present invention there is provided a mass spectrometer comprising:
a device for separating ions according to their ion mobility or rate of change of ion mobility with electric field strength;
wherein in a mode of operation at a first time ions are passed in a first direction through the device and wherein at a second later time ions are passed in second direction through the device, wherein the second direction is different or opposed to the first direction.

According to an aspect of the present invention there is provided a method of mass spectrometry comprising:

separating ions according to their ion mobility or rate of change of ion mobility with electric field strength in a device; and
passing ions at a first time in a first direction through the device and passing ions at a second later time in a second direction through the device, wherein the second direction is different or opposed to the first direction.

According to an aspect of the present invention there is provided a mass spectrometer comprising:
a device for separating ions according to their ion mobility or rate of change of ion mobility with electric field strength;
an ion trap or ion guide which is arranged to receive ions emerging from the device and which are being transmitted in a first direction; and
acceleration means arranged and adapted to cause ions emerging from the device to be fragmented or to react upon entering the ion trap or ion guide so that a plurality of fragment, daughter, product or adduct ions are formed;
wherein in a mode of operation at least some of the plurality of fragment, daughter, product or adduct ions are transmitted or passed from the ion trap or ion guide to the device in a second direction which is different from or opposed to the first direction.

According to an aspect of the present invention there is provided a method of mass spectrometry comprising:
separating ions according to their ion mobility or rate of change of ion mobility with electric field strength in a device; and
providing an ion trap or ion guide which is arranged to receive ions emerging from the device and which are being transmitted in a first direction;
accelerating ions emerging from the device so that the ions are fragmented or react upon entering the ion trap or ion guide so that a plurality of fragment, daughter, product or adduct ions are formed; and
transmitting or passing at least some of the plurality of fragment, daughter, product or adduct ions from the ion trap or ion guide to the device in a second direction which is different from or opposed to the first direction.

According to another aspect of the present invention there is provided a mass spectrometer comprising:
a first ion trap or ion guide;
a device for separating ions according to their ion mobility or rate of change of ion mobility with electric field strength, the device being arranged downstream of the first ion trap or ion guide;
a second ion trap or ion guide arranged downstream of the first ion trap or guide;
wherein in a mode of operation ions are passed from the first ion trap or ion guide to the device and onwards to the second ion trap or ion guide whereupon at least some of the ions or at least some fragment, daughter, product or adduct ions derived from the ions are then passed from the second ion trap or ion guide to the device and onwards to the first ion trap or ion guide.

According to another aspect of the present invention there is provided a method of mass spectrometry comprising:
providing a first ion trap or ion guide;
providing a device for separating ions according to their ion mobility or rate of change of ion mobility with electric field strength, the device being arranged downstream of the first ion trap or ion guide;
providing a second ion trap or ion guide arranged downstream of the first ion trap or guide; and passing ions from the first ion trap or ion guide to the device and onwards to the second ion trap or ion guide; and then passing at least some of the ions or at least some fragment, daughter, product or adduct ions derived from the ions from the second ion trap or ion guide to the device and onwards to the first ion trap or ion guide.

According to the preferred embodiment a mass spectrometer is provided which comprises only a relatively few stages. However, the mass spectrometer is preferably nonetheless capable of performing relatively complex experiments which conventionally would require a mass spectrometer comprising a greater number of stages to perform. For example, a mass spectrometer according to an embodiment of the present invention comprising LC-IMS-MS stages is preferably able to perform similar experiments to those which may be performed using a conventional mass spectrometer comprising LC-IMS-IMS-MS or LC-IMS-CID-IMS-MS stages.

A mass spectrometer according to the preferred embodiment preferably comprising a single ion mobility separation stage is preferably also able to perform particularly complex experiments which would conventionally require a mass spectrometer comprising, for example, LC-IMS-CID-IMS-CID-MS stages to perform wherein second generation fragment or daughter ions are produced and are subsequently mass analysed.

The conventional approach to designing a mass spectrometer has been to provide multiple ion mobility separation and ion fragmentation stages in series. Ions pass sequentially through multiple stages from one stage of the mass spectrometer to the next. The number of ion mobility separation and ion fragmentation stages which need to be provided is determined by the desired capability of the mass spectrometer. The conventional approach leads to a mass spectrometer comprising a large number of discrete stages and which is relatively lengthy and complex. The mass spectrometer design is relatively inflexible and the range of experiments that can be performed by such a conventional mass spectrometer is limited by the number and arrangement of the various stages. A conventional mass spectrometer comprising a single ion fragmentation stage is not, for example, able to produce second generation fragment or daughter ions. In addition when only part of the capability of a mass spectrometer is utilised (e.g. an LC-IMS-MS analysis is required using a mass spectrometer comprising LC-IMS-CID-IMS-MS stages) then the extra stages are unnecessary and can compromise performance. For example, the elution profile of an ion species leaving a first ion mobility separation region may not be able to be measured directly since the ions may have to pass through an additional ion mobility separation region before reaching an ion detector. Conventional mass spectrometers comprising numerous multiple stages in series also require a more complex calibration procedure and this can lead to less certainty in the results.

A mass spectrometer according to the preferred embodiment preferably enables a more compact and substantially more flexible mass spectrometer to be provided. A particularly preferred aspect of the present invention is that ions in a mode of operation are passed back upstream at least once through a single ion mobility separation stage or section.

According to an embodiment a mass spectrometer is preferably provided comprising an ionisation source and an ion mobility spectrometer or separator comprising an RF ion guide wherein ions are confined near to the central axis. Ions are preferably propelled along the length of the ion mobility spectrometer or separator from one end to the other end in either direction. The mass spectrometer preferably further comprises an ion detector.

In a preferred embodiment ions are preferably propelled along the axis of the ion mobility spectrometer or separator first in one direction (e.g. downstream) and then preferably in the opposite or reverse direction (e.g. upstream). The ions are preferably separated according to their ion mobility in at least one pass through the length of the ion mobility spectrometer or separator. Each time ions are passed along or through the length of the ion mobility spectrometer or separator the ions may or may not be separated according to their ion mobility.

In one embodiment the ion mobility spectrometer or separator may comprise a drift tube comprising an RF ion guide wherein an axial DC voltage gradient is preferably maintained along the length of the ion guide. The direction of the axial DC voltage gradient may preferably be reversed when it is desired to cause ions to separate according to their ion mobility in the reverse direction.

In another embodiment the ion mobility spectrometer or separator may comprise an RF ion guide wherein one or more transient DC potentials or voltages or DC potential or voltage waveforms are applied to the electrodes of the ion guide. The one or more transient DC voltages or potentials or DC voltage or potential waveforms are preferably initially applied to the electrodes of the ion guide so that ions are urged in a first (e.g. downstream) direction. The one or more transient DC voltages or potentials or DC voltage or potential waveforms may then be applied to the electrodes of the ion guide so as to urge ions in a second opposite direction (e.g. upstream).

According to the preferred embodiment ions may be trapped in at least one region, ion trap or ion guide. For example, a first ion trap may be located upstream of an ion mobility spectrometer or separator. A second ion trap may be located downstream of the ion mobility spectrometer or separator. Ions are preferably accumulated and trapped in either the first ion trap and/or the second ion trap before the ions are then preferably released and passed through the ion mobility spectrometer or separator. In an embodiment ions are preferably trapped in the first ion trap or ion guide and/or the second ion trap or ion guide such that one or more groups of ions are spatially separated along the central axis of the ion trap and such that the ions are fractionated or provided in separate packets of ions which preferably remain isolated from each other. One or more of the isolated packets of ions may then be retained within the ion trap whilst one or more other packets of ions may be discarded from the ion trap.

In one embodiment ions are preferably fragmented. Ions may be fragmented in a region or ion trap arranged either upstream and/or downstream of the ion mobility spectrometer or separator. Ions may also be fragmented either before or after they have passed through the ion mobility spectrometer or separator.

BRIEF DESCRIPTION OF THE DRAWINGS

Various embodiments of the present invention will now be described, by way of example only, and with reference to the accompanying drawings in which:

FIG. 2 shows an ion mobility spectrum of a group of ions and their associated drift time through an ion mobility spectrometer or separator;

FIG. 3A shows the ion mobility spectrum as shown in FIG. 2 and indicates three drift time regions, FIG. 3B shows a mass spectrum of ions observed between drifts times O and time T1, FIG. 3C shows a mass spectrum of ions observed between drift times T1 and T2 and FIG. 3D shows a mass spectrum of ions observed subsequent to drift time T2;

FIG. 4 shows an embodiment of the present invention wherein two additional electrode assemblies are provided and wherein the second ion trap or ion guide is located in a separate vacuum chamber;

DETAILED DESCRIPTION OF THE PREFERRED EMBODIMENTS

Figure 1:
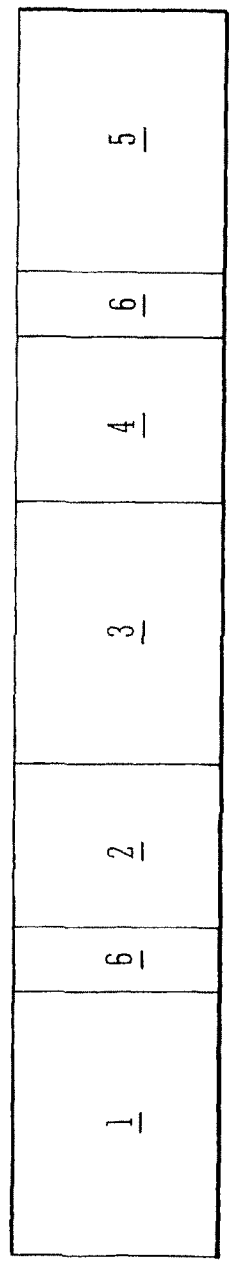
FIG. 1 shows an embodiment of the present invention wherein a first ion trap is provided upstream of an ion mobility spectrometer or separator and a second ion trap is provided downstream of the ion mobility spectrometer or separator to receive ions which emerge from the ion mobility spectrometer or separator.

A preferred embodiment of the present invention will now be described with reference to FIG. 1. FIG. 1 shows a schematic arrangement of a mass spectrometer according to an embodiment of the present invention comprising an ion source 1 and a first ion trap 2 or means of collecting, storing and releasing ions 2 arranged downstream of the ion source 1. An ion mobility spectrometer or separator 3 is preferably arranged downstream of the first ion trap 2. A second ion guide or ion trap 4 is preferably arranged downstream of the ion mobility spectrometer or separator 3. The second ion guide or ion trap 4 preferably comprises a second means of collecting, storing and releasing ions. A mass analyser 5 is preferably arranged downstream of the second ion or ion trap 4 and the ion mobility separator or spectrometer 3.

The ion source 1 may comprise a pulsed ion source such as a Laser Desorption Ionisation ("LDI") ion source, a Matrix Assisted Laser Desorption/Ionisation ("MALDI") ion source or a Desorption/Ionisation on Silicon ("DIOS") ion source. Alternatively, the ion source 1 may comprise a continuous ion source 2 such as an Electrospray Ionisation ("ESI") ion source, an Atmospheric Pressure Chemical Ionisation ("APCI") ion source, an Electron Impact ("EI") ion source, an Atmospheric Pressure Photon Ionisation ("APPI") ion source, a Desorption Electrospray Ionisation ("DESI") ion source, an Atmospheric Pressure MALDI ("AP-MALDI") ion source, a Chemical Ionisation ("CI") ion source, a Fast Atom Bombardment ("FAB") ion source, a Liquid Secondary Ion Mass Spectrometry ("LSIMS") ion source, a Field Ionisation ("FI") ion source or a Field Desorption ("FD") ion source. Other continuous or pseudo-continuous ion sources may also be used.

A differential pumping aperture 6 is preferably provided between the ion source 1 and the first ion trap or ion guide 2. A differential pumping aperture is also preferably provided between the second ion trap or ion guide 4 and the mass analyser 5. According to an embodiment the first ion trap or ion guide 2, the ion mobility spectrometer or separator 3 and the second ion trap or ion guide 4 are provided in the same vacuum chamber.

A mass filter (not shown) such as a quadrupole rod set mass filter, a Wein filter, a Time of Flight mass analyser or a magnetic sector mass analyser may optionally be provided between the ion source 1 and the first ion trap or ion guide 2. The mass filter may be arranged in a mode of operation to select certain parent or precursor ions for onward transmission to the first ion trap or ion guide 2 and to attenuate other ions.

Ions are preferably collected and stored in the first ion trap or ion guide 2. The first ion trap or ion guide 2 is preferably maintained at a pressure between $10^{-4}$ mbar and 100 mbar, further preferably between $10^{-3}$ and 10 mbar. The first ion trap or ion guide 2 preferably comprises an RF ion guide wherein ions are confined close to the central axis when undergoing collisions with background gas molecules.

The first ion trap or ion guide 2 preferably comprises a stacked ring or ion tunnel RF ion guide comprising a plurality of electrodes having apertures through which ions are preferably transmitted in use. Opposite phases of an AC or RF voltage are preferably applied to neighbouring or adjacent ring electrodes so that ions are preferably radially confined within the first ion trap or ion guide 2 by a radial pseudo-potential well. One or more transient DC potentials or voltages or DC potential or voltage waveforms are preferably applied or superimposed to the electrodes forming the first ion trap or ion guide 2 so that in a mode of operation ions are preferably urged along the length of the first ion guide or ion trap 2. Ions are preferably trapped in discrete real axial potential wells which are preferably formed within the first ion guide or ion trap 2 and which are preferably translated or moved along the length of the first ion guide or ion trap 2.

According to another embodiment the first ion trap or ion guide may comprise a sandwich plate RF ion trap or ion guide comprising a plurality of electrodes arranged generally in the plane of ion transmission. AC or RF voltages and optionally DC voltages may be applied to the electrodes of the ion trap or ion guide in order to confine ions radially within the ion trap or ion guide.

The first ion trap or ion guide 2 may alternatively comprise an ion funnel ion guide comprising a plurality of electrodes each having an aperture through which ions are transmitted in use. The diameter or size of the apertures of the electrodes preferably taper in one direction along the length of the ion funnel ion guide.

According to another embodiment the first ion guide or ion trap 2 may comprise a quadrupole, hexapole, octapole or higher order multipole rod set ion guide. The first ion trap or ion guide 2 may be segmented axially into a plurality of axial segments.

The first ion trap or ion guide 2 is preferably arranged to store ions received from the ion source 1 and to release ions in one or more pulses into the ion mobility spectrometer or separator 3 which is preferably arranged downstream of the first ion trap or ion guide 2. A plate or electrode may be provided (not shown) at the exit of the first ion trap or ion guide 2. The plate or electrode may be maintained at a potential such that a potential barrier is preferably created which preferably prevents ions from exiting the first ion trap or ion guide 2. For positive ions the plate or exit electrode may be maintained at a potential of approximately +10 V with respect to the DC potential at which the other electrodes forming the first ion trap or ion guide 2 are maintained in order to prevent ions from exiting the first ion guide or ion trap 2. If the potential on the plate or electrode at the exit of the first ion guide or ion trap 2 is momentarily lowered to 0 V, or less than 0 V, with respect to the potential at which the other electrodes forming the first ion trap or ion guide 2 are maintained, then ions will preferably be released from the first ion guide or ion trap 2 in a pulse into or towards the ion mobility spectrometer or separator 3.

According to an embodiment the first ion trap or ion guide 2 preferably comprises a plurality of electrodes wherein the apertures of the electrodes are preferably all the same size. In other embodiments at least 60%, 65%, 70%, 75%, 80%, 85%, 90% or 95% of the electrodes may have apertures which are substantially the same size. Adjacent electrodes are preferably connected to opposite phases of an AC or RF supply so that a radial pseudo-potential well is created which acts to confine ions radially within the first ion trap or ion guide 2.

One or more transient DC potentials or voltages or DC potential or voltage waveforms are preferably superimposed onto the electrodes forming the first ion trap or ion guide 2 in a mode of operation. The one or more transient DC voltages or potentials or DC potential or voltage waveforms are preferably applied to the electrodes of the first ion trap or ion guide 2 so that one or more real potential barriers are formed or created along the length of the first ion trap or ion guide 2. The one or more transient DC voltages or potentials or DC potential or voltage waveforms are preferably progressively applied to a succession of electrodes of the first ion trap or ion guide 2 such that the one or more real potential barriers preferably move along or are translated along the axis of the first ion trap or ion guide 2. Ions may in a mode of operation be propelled or urged in a downstream direction towards the ion mobility spectrometer or separator 3 and the mass analyser 5. In another mode of operation ions may be urged in an opposite direction i.e. upstream towards the ion source 1.

The first ion trap or ion guide 2 is preferably provided in a vacuum chamber that is preferably maintained, in use, at a pressure within the range 0.001-10 mbar. The gas pressure within the first ion trap or ion guide 2 is preferably sufficient to impose collisional damping of ion motion but is preferably not sufficient so as to impose excessive viscous drag upon the movement of ions. The amplitude and average velocity of the one or more potential barriers which are preferably translated along the length of the first ion trap or ion guide 2 in a mode of operation is preferably set such that ions are preferably unable to slip over the one or more potential hills or barriers. Ions are therefore preferably transported ahead of each potential barrier which is translated along the length of the first ion trap or ion guide 2 regardless of the mass, mass to charge ratio or ion mobility of the ion.

The ion mobility spectrometer or separator 3 which is preferably provided downstream of the first ion guide or ion trap preferably comprises a device which in a mode of operation causes ions to become temporally separated according to their ion mobility. The ion mobility spectrometer or separator 3 may comprise one of several different forms.

The ion mobility spectrometer or separator 3 may comprise a drift tube wherein a number of guard rings are distributed within the drift tube. The guard rings are preferably interconnected by equivalent valued resistors and are preferably connected to a DC voltage source. A linear DC voltage gradient is preferably generated or maintained along the length of the drift tube. According to this embodiment ions may not be confined radially within the ion mobility spectrometer or separator 3.

According to another embodiment the ion mobility spectrometer or separator 3 may comprise a plurality of ring, annular or plate electrodes. The electrodes preferably each have an aperture therein through which ions are preferably transmitted in use. The apertures are preferably all the same size and are preferably circular. In other embodiments at least 60%, 65%, 70%, 75%, 80%, 85%, 90% or 95% of the electrodes preferably have apertures that are substantially the same size or area.

The ion mobility spectrometer or separator 3 may comprise a plurality of electrodes arranged in a discrete vacuum chamber. The ion mobility spectrometer or separator 3 preferably has a length of between 100 mm and 200 mm. The ion mobility spectrometer or separator 3 is preferably provided in a vacuum chamber that is preferably maintained, in use, at a pressure within the range 0.1-10 mbar.

Alternate electrodes forming the ion mobility spectrometer or separator 3 are preferably coupled to opposite phases of an AC or RF voltage supply so that ions are preferably confined radially within the ion mobility spectrometer or separator in a radial pseudo-potential well. The AC or RF voltage supply preferably has a frequency within the range 0.1-3.0 MHz, preferably 0.3-2.0 MHz, further preferably 0.5-1.5 MHz.

According to an embodiment the electrodes comprising the ion mobility spectrometer or separator 3 may be interconnected via resistors to a DC voltage supply which may, for example, comprise a 400 V supply. The resistors interconnecting the electrodes forming the ion mobility spectrometer or separator 3 may be substantially equal in value so that a linear axial DC voltage gradient is preferably maintained along the length of the ion mobility spectrometer or separator 3.

According to an embodiment the DC voltage gradient maintained along the length of the ion mobility spectrometer or separator 3 may have a linear, non-linear, continuous or stepped profile. The DC voltage gradient may according to an embodiment be arranged in a mode of operation so as to propel, drive, force or urge ions in a downstream direction towards the mass analyser 5. The direction of the DC voltage gradient may be switched, or reversed in use, so that ions may be urged in a mode of operation in the opposite direction e.g. in an upstream direction towards the ion source 1. The AC or RF voltage which is preferably applied to the electrodes forming the ion mobility spectrometer or separator 3 is preferably superimposed upon the DC voltage applied to the electrodes and preferably serves to cause ions to be confined radially within the ion mobility spectrometer or separator 3 within a radial pseudo-potential well.

According to a preferred embodiment the ion mobility spectrometer or separator 3 preferably comprises an ion guide comprising a plurality of electrodes each having an aperture through which ions are transmitted. One or more transient DC voltages or potentials or one or more transient DC voltage or potential waveforms are preferably applied to the electrodes. The apertures of the electrodes forming the ion mobility spectrometer or separator 3 are preferably all the same size. In other embodiments at least 60%, 65%, 70%, 75%, 80%, 85%, 90% or 95% of the electrodes have apertures that are substantially the same size. Adjacent electrodes are preferably connected to the opposite phases of an AC or RF supply so that ions are confined radially within the ion mobility spectrometer or separator.

The one or more transient DC voltages or potentials or one or more transient DC voltage or potential waveforms which are preferably applied to the electrodes of the ion mobility spectrometer or separator 3 preferably cause one or more real potential hills or barriers to be created which are then preferably translated or moved along the axis of the ion mobility spectrometer or separator 3. The one or more transient DC voltages or potentials or DC voltage or potential waveforms are preferably progressively applied to a succession of electrodes of the ion mobility spectrometer or separator 3 in such a way that one or more real potential hills or barriers preferably move along or are translated along the axis or length of the ion mobility spectrometer or separator 3. In a mode of operation ions are preferably driven or urged downstream towards the mass analyser 5. In another mode of operation ions are preferably driven or urged in a reverse direction upstream towards the ion source 1.

The ion mobility spectrometer or separator 3 is preferably provided in a vacuum chamber that is preferably maintained, in use, at a pressure within the range 0.1-10 mbar. The presence of gas within the ion mobility spectrometer or separator 3 preferably imposes a viscous drag upon the movement of ions. The amplitude and average velocity of the one or more real potential hills or barriers which are preferably formed and translated along the length of the ion mobility spectrometer or separator 3 is preferably arranged to be such that some ions will slip over the one or more potential hills or barriers as they are translated along the length of the ion mobility spectrometer or separator 3. The lower the mobility of an ion the more likely it is that the ion will slip over a potential hill or barrier which is being translated along the length of the ion mobility spectrometer or separator 3. As a result ions having different ion mobilities will preferably be transported at different velocities or rates along and through the length of the ion mobility spectrometer or separator 3 and will therefore preferably be separated according to their ion mobility.

The typical drift times of ions through the preferred ion mobility spectrometer or separator 3 may be of the order of 2-50 ms. According to a preferred embodiment ions may take between 5 and 20 ms to pass through or along the length of the ion mobility spectrometer or separator 3.

According to the preferred embodiment ions preferably exit the ion mobility spectrometer or separator 3 and then preferably pass to or are received by a second ion trap or ion guide 4 which is preferably arranged downstream of the ion mobility spectrometer or separator 3. The second ion trap or ion guide 4 is preferably substantially similar to the first ion trap or ion guide 2 arranged upstream of the ion mobility spectrometer or separator 3. The second ion trap or ion guide 4 preferably comprises a stacked ring or ion tunnel RF ion guide comprising a plurality of electrodes having apertures through which ions are transmitted in use. Opposite phases of an AC or RF voltage are preferably applied to neighbouring electrodes of the second ion trap or ion guide 4 so that ions are preferably confined radially within the second ion trap or ion guide 4 within a radial pseudo-potential well.

One or more transient DC voltages or potentials or DC voltage or potential waveforms are preferably applied to the electrodes of the second ion trap or ion guide 4 in order to urge ions along the length of the second ion guide or ion trap 4. Ions are preferably trapped in discrete real axial potential wells within the second ion trap or ion guide 4. In a mode of operation the real axial potential wells may be translated in a downstream direction towards the mass analyser 5. In another mode of operation the real axial potential wells formed within the second ion trap or ion guide 4 may be translated in a reverse direction so that ions are preferably translated in an upstream direction and pass to the ion mobility spectrometer or separator 3. In this mode of operation the ion mobility spectrometer or separator then preferably passes the ions back further upstream to the first ion guide or ion trap 2.

According to a less preferred embodiment the second ion trap or ion guide 4 may comprise an alternative form of ion guide such as an AC or RF ion guide or ion trap comprising a plurality of planar, plate or mesh electrodes arranged generally in the plane of ion travel. AC or RF voltages and optionally DC voltages may be applied to the electrodes of the ion guide or ion trap in order to confine ions radially within the ion trap or ion guide.

Other embodiments are contemplated wherein the second ion trap or ion guide 4 may comprise an ion funnel ion guide comprising a plurality of electrodes having apertures. The diameter or size of the apertures preferably tapers in size along the length of the ion trap or ion guide.

According to another embodiment the second ion trap or ion guide 4 may comprise a quadrupole, hexapole, octapole or other higher order multipole rod set ion guide. The second ion trap or ion guide 4 may be axially segmented into a plurality of axial segments.

The apertures of the electrodes forming the second ion trap or ion guide 4 are preferably all the same size. In other embodiments at least 60%, 65%, 70%, 75%, 80%, 85%, 90% or 95% of the electrodes have apertures which are substantially the same size. The second ion trap or ion guide 4 is preferably provided in a vacuum chamber that is preferably maintained, in use, at a pressure within the range 0.001-10 mbar.

The second ion trap or ion guide 4 may, in a mode of operation, be arranged to store ions and may then release ions in pulses or packets. A plate or electrode (not shown) may be arranged at the exit of the second ion trap or ion guide 4. The plate or electrode may be maintained at a potential such that a potential barrier is preferably created which substantially prevents ions from exiting the second ion trap or ion guide 4. If the potential on the plate or electrode at the exit of the second ion trap or ion guide 4 is momentarily lowered then ions may be released in a pulse from the second ion trap or ion guide 4.

According to the preferred embodiment a mass analyser 5 is preferably arranged downstream of the second ion guide or ion trap 4. The mass analyser 5 preferably comprises an orthogonal acceleration Time of Flight mass analyser. Alternatively, the mass analyser 5 may comprise an axial acceleration Time of Flight mass analyser, a quadrupole rod set mass filter or mass analyser, a 3D quadrupole ion trap, a linear quadrupole ion trap, a magnetic sector mass analyser, an Ion Cyclotron Resonance mass analyser or an orbitrap mass analyser. The mass analyser 5 may also comprise variations of the aforementioned types of mass analyser which employ Fourier Transforms of mass dependant resonance frequencies and any combination thereof.

According to an embodiment of the present invention ions are preferably produced in the ion source 1 upstream of the first trap or ion guide 2. The ions are then preferably accumulated and stored in the first ion trap or ion guide 2. A group of ions is then preferably periodically released from the first ion trap or ion guide 2 and the ions preferably pass into the ion mobility spectrometer or separator 3. The ion mobility spectrometer or separator 3 is preferably arranged to receive the group of ions and preferably separates the ions according to their ion mobility. The ions preferably progress along the central axis of the ion mobility spectrometer or separator 3 and are temporally separated according to their ion mobility.

FIG. 2 shows an ion mobility spectrum of a number of fragment ions which resulted from the fragmentation of the doubly protonated ion $(M+2H)^{2+}$ having a mass to charge ratio 785.8 and which was derived from the peptide Glu-Fibrinopeptide B. As can be seen from FIG. 2, ions having relatively low mass to charge ratios take a relatively short period time to drift or pass along or through the ion mobility spectrometer or separator 3 whereas ions having a relatively high mass to charge ratio take a substantially longer time to drift or pass along or through the ion mobility spectrometer or separator 3.

The ions exiting the ion mobility spectrometer or separator 3 are preferably received by or into the second ion trap or ion guide 4. The second ion trap or ion guide 4 is preferably arranged to collect and isolate one or more components, fractions or packets of ions which have been separated by the ion mobility spectrometer or separator 3 and which preferably emerge from the ion mobility spectrometer or separator 3 at different times. The second ion trap or ion guide 4 preferably comprises an ion guide comprising a plurality of electrodes having apertures and wherein one or more transient DC voltages or potentials or DC voltage or potential waveforms is applied to the electrodes in a mode of operation. The one or more transient DC voltages or potentials or DC voltage or potential waveforms applied to the electrodes of the second ion trap or ion guide 4 is preferably synchronised with the release of ions from the first ion trap or ion guide 2. Preferably, some or all of the ions that have been separated by the ion mobility spectrometer or separator 3 according to their ion mobility are received by the second ion trap or guide 4 and separate packets of ions are preferably trapped within separate portions, sections or axial trapping regions formed within the second ion trap or ion guide 4. For example, ions that arrive at the second ion trap or ion guide 4 before a certain first drift time T1 may be arranged to be collected or trapped within a first series of real axial potential wells formed or created within the second ion trap or ion guide 4. Ions that arrive at the second ion trap or ion guide 4 after the first drift time T1 and before a second later drift time T2 may be arranged to be collected or trapped within a second different series of real axial potential wells formed or created within the second ion trap or ion guide 4. Ions that arrive at the second ion trap or ion guide 4 after the second drift time T2 may be arranged to be collected or trapped within a third yet further different series of real axial potential wells formed or created within the second ion trap or ion guide 4.

FIGS. 3A-3D illustrate the different components, fractions or packets of ions which emerge from the ion mobility spectrometer or separator 3 at different times. FIG. 3A shows an ion spectrum of the various different fragment ions as illustrated in FIG. 2 and indicates two drift times T1 and T2. FIG. 3B shows a mass spectrum of ions which emerge from the ion mobility spectrometer or separator 3 between drift times 0 and T1 and which have relatively low mass to charge ratios. FIG. 3C shows a mass spectrum of ions which emerge from the ion mobility spectrometer or separator 3 between drift times T1 and T2 and which have intermediate mass to charge ratios. FIG. 3D shows a mass spectrum of ions which emerge from the ion mobility spectrometer or separator 3 subsequent to drift time T2 and which have relatively high mass to charge ratios. It will be appreciated that ions of interest having a specific drift time through the ion mobility spectrometer or separator 3 are preferably arranged to be collected and trapped in one or more specific real axial potential well(s) formed or created within the second ion trap or ion guide 4. The ions are preferably isolated from other ions which have different drift times through the ion mobility spectrometer or separator 3.

Once ions have been received and trapped within a series of separate real axial potential wells formed or created within the second ion trap or ion guide 4, the transient DC voltages or potentials which are preferably applied to the electrodes of the ion mobility spectrometer or separator 3 may then be applied in the opposite direction so as to urge ions in the opposite direction i.e. the real axial potential wells may be translated in an upstream direction back towards the ion source 1. The axial potential wells formed within the second ion trap or ion guide 4 are preferably also translated in the opposite direction i.e. in a direction back towards the ion source 1.

According to an embodiment ions trapped in one or more axial potential wells within the second ion trap or ion guide 4 which are not of potential interest may be discarded by, for example, temporarily removing the AC or RF voltage applied to the electrodes adjacent the one or more axial potential wells in question so that the ions within these one or more axial potential wells are now no longer confined radially. The ions are therefore allowed to disperse and are effectively lost. Alternatively, ions which are not of interest may be allowed to pass back into the ion mobility spectrometer or separator 3 but may then be discarded within the ion mobility spectrometer or separator 3. Ions may be discarded within the ion mobility spectrometer or separator 3 by temporarily removing the AC or RF voltage applied to some of the electrodes of the ion mobility spectrometer or separator 3 or a section of the ion mobility spectrometer or separator 3 so that ions which are not of interest are no longer confined radially within the ion mobility spectrometer or separator 3. These ions are then allowed to disperse and are effectively lost. Other alternative means by which the ions may be discarded either within the ion mobility spectrometer or separator 3 and/or the first ion trap or ion guide 2 and/or the second ion trap or ion guide 4 are also contemplated.

According to an embodiment a first group of ions which are of potential interest and which are trapped in an axial potential well within the second ion trap or ion guide 4 are preferably released from the second ion trap or ion guide 4 in an upstream direction towards the ion mobility spectrometer or separator 3. The ions are preferably arranged to pass through the ion mobility spectrometer or separator 3 which in a mode of operation may be arranged to operate in an ion guide only mode of operation so that ions are onwardly transmitted through the ion mobility spectrometer or separator 3 without being separated according to their ion mobility. Once the ions have passed through the ion mobility spectrometer or separator 3 the ions are then preferably collected or trapped in one or more real axial potential wells which are preferably formed or created within the first ion trap or ion guide 2. A second group of ions trapped in the next axial potential well within the second ion trap or ion guide 4 may then preferably be released from the second ion trap or ion guide and this group of ions may then preferably be arranged to pass in an upstream direction into the ion mobility spectrometer or separator 3. The second group of ions may then also preferably be arranged to pass through the ion mobility spectrometer or separator 3 without being separated according to their ion mobility. The second group of ions is then preferably collected and trapped in one or more separate real axial potential wells formed or created within the first ion trap or ion guide 2. The process may be repeated multiple times so that multiple packets of ions are preferably transferred from the second ion trap or ion guide to the first ion trap or ion guide 2 via the ion mobility spectrometer or separator 3. Packets of ions may then preferably be released in turn from the first ion trap or ion guide 2 such that ions preferably pass back through the ion mobility spectrometer or separator 3 and are preferably further separated according to their ion mobility.

According to a preferred aspect of the present invention ions may be passed back and forth through the ion mobility spectrometer or separator 3 a plurality of times as required. Once ions have been sufficiently separated according to their ion mobility the ions are then preferably onwardly transmitted or transported by the second ion trap or ion guide 4 (which preferably operates in a non-trapping or ion guide only mode of operation) to the mass analyser 5.

According to an embodiment the potential difference which is preferably maintained between the ion mobility spectrometer or separator 3 and the second ion guide or ion trap 4 may in a mode of operation be increased with time such that ions are induced to fragment in an optimum manner as they are accelerated out of the exit of the ion mobility spectrometer or separator 3 and into the second ion trap or guide 4. In this mode of operation the ions are preferably caused to fragment or react upon entering the second ion guide or ion trap 4. The resulting fragment or daughter ions are preferably trapped in one or more real axial potential wells formed or created within the second ion trap or guide 4. Fragment or daughter ions which correspond to different parent or precursor ions which emerged from the ion mobility spectrometer or separator 3 at different times are preferably collected and isolated in separate real axial potential wells within the second ion trap or ion guide 4.

Once all parent or precursor ions have emerged from the ion mobility spectrometer or separator 3 and have been fragmented into a plurality of fragment or daughter ions, then all the fragment or daughter ions corresponding to a particular parent or precursor ion may then preferably be separated according to their ion mobility by passing the group of fragment or daughter ions in the reverse direction back upstream to the ion mobility spectrometer or separator 3. The fragment or daughter ions are then preferably separated according to their ion mobility as they pass upstream through the ion mobility spectrometer or separator 3 towards the first ion trap or ion guide 2. Alternatively, the fragment or daughter ions may simply be transported or guided through the ion mobility spectrometer or separator 3 without being separated according to their ion mobility i.e. the ion mobility spectrometer or separator 3 may be operated in an ion guiding only mode of operation.

The process of separating ions into ion mobility fractions, fragmenting the ions which emerge from the ion mobility spectrometer or separator 3 and trapping and isolating one or more fractions of fragment or daughter ions may be repeated a number of times. As a result second, third, fourth and higher generation fragment, daughter, product or adduct ions may be produced by varying the number passes of ions through the ion mobility spectrometer or separator 3 and varying the number of fragmentation cycles. At the end of each cycle of operation ions exiting the ion mobility spectrometer or separator 3 are preferably transported by the second ion trap or ion guide 4 to the mass analyser 5 for subsequent mass analysis.

Figure 4:
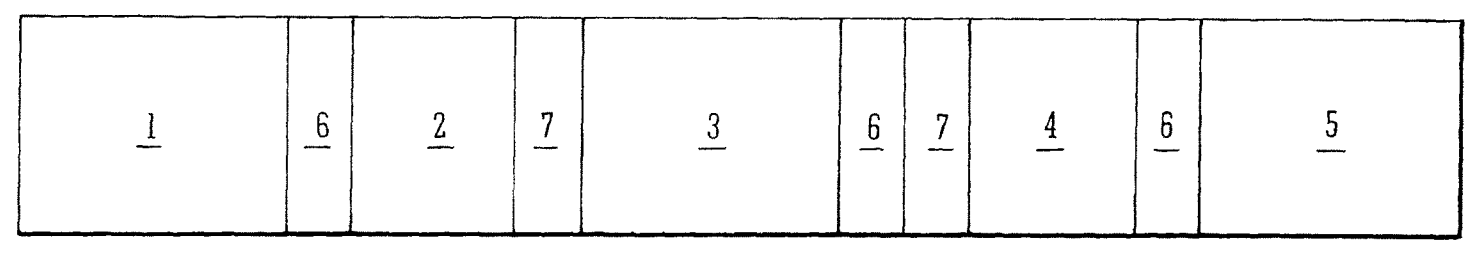

Another embodiment of the present invention is shown in FIG. 4. According to this embodiment an electrode assembly 7 is preferably provided between the first ion trap or ion guide 2 and the ion mobility spectrometer or separator 3. An electrode assembly 7 is also preferably provided between the ion mobility spectrometer or separator 3 and the second ion trap or ion guide 4.

One or both of the electrode assemblies 7 preferably function as a deflection system to divert ions away from the central axis so that ions are then effectively lost to the system. According to another embodiment one or both of the electrode assemblies 7 may function as an ion gate which allows ions to pass through the ion gate in a mode of operation and which preferably prevent ions from passing through the ion gate in another mode of operation. The ion gate may function by applying a suitable potential to the electrode assembly 7 so that a potential barrier exists which substantially prevents ions from passing beyond the potential barrier. The potential barrier can then be removed for a controlled period of time to allow certain ions to pass therethrough.

One or both of the electrode assemblies 7 are preferably capable of being switched quickly between the two modes of operation. One or both of the electrode assemblies 7 can preferably be switched quickly enough to allow only some ions which have been separated according to their ion mobility by the ion mobility spectrometer or separator 3 to pass and to prevent or attenuate other ions which are emerging from the ion mobility spectrometer or separator 3. With reference back to FIG. 3, an electrode assembly 7 provided downstream of the ion mobility spectrometer or separator 3 may, for example, be arranged to have a zero or 0% transmission efficiency between drift times 0 to T1 in order to block or attenuate ions which emerge from the ion mobility spectrometer or separator 3 during these times. The electrode assembly 7 may then be switched so as to have a full or 100% transmission efficiency between drift times T1 and T2 in order to transmit all ions which emerge from the ion mobility spectrometer or separator 3 between these two times. The electrode assembly 7 may then be switched back to have a zero or 0% transmission efficiency for the remainder of the ion mobility separation cycle in order to block or attenuate ions which emerge from the ion mobility spectrometer or separator 3 after drift time T2. As a result the second ion trap or ion guide 4 will only receive and trap ions which were transmitted through the ion mobility spectrometer or separator 3 between drift times T1 and T2 and which therefore have intermediate mass to charge ratios.

An electrode assembly 7 may also be placed at the entrance of the ion mobility spectrometer or separator 3 as shown in FIG. 4. This enables drift time selection to be performed when ions are transmitted back upstream through the ion mobility spectrometer separator 3 towards the first ion trap or ion guide 2. Various alternative systems of removing or attenuating ions as they emerge from the ion mobility spectrometer or separator 3 prior to entering into the first ion trap or ion guide 2 and/or the second ion trap or ion guide 4 are also contemplated.

According to an embodiment a further differential pumping aperture 6 may be provided between the ion mobility spectrometer or separator 3 and the second ion trap or ion guide 4 as shown in FIG. 4. The further differential pumping aperture 6 in combination with the differential pumping aperture 6 arranged between the second ion trap or ion guide 4 and the mass analyser 5 preferably allows the second ion trap or ion guide 4 to be maintained at a substantially lower pressure than that of the ion mobility spectrometer or separator 3. According to an embodiment the ion mobility spectrometer or separator 3 may be maintained at a pressure in the range 0.1 mbar to 10 mbar. The second ion trap or ion guide 4 may, in contrast, be maintained at a relatively lower pressure in the range 0.001 to 0.1 mbar. By maintaining the second ion trap or ion guide 4 at a lower pressure than that of the ion mobility spectrometer or separator 3 the second ion trap or ion guide 4 may be used more effectively to induce fragmentation of ions by Collision Induced Decomposition than if it were maintained at the same relatively high pressure as the ion mobility spectrometer or separator 3. The mass analyser 5 is preferably maintained at a relatively low pressure $<10^{-4}$ mbar.

The ion mobility spectrometer or separator 3 may in a mode of operation be arranged to operate as an ion guide so as to transmit ions either upstream towards the first ion trap or ion guide 2 or downstream towards the second ion trap or ion guide 4 without substantially separating the ions according to their ion mobility. This may according to one embodiment be achieved by, for example, lowering the gas pressure within the ion mobility spectrometer or separator 3 to a pressure of 0.01 mbar or less.

According to an embodiment one or more transient DC voltages or potentials or DC potential or voltage waveforms may be applied to the electrodes of the ion mobility spectrometer or separator 3 in order to cause a plurality of real axial potential wells or barriers to be created which preferably act to transport or translate ions along the length of the ion mobility spectrometer or separator 3 without causing the ions to be separated according to their ion mobility. According to this mode of operation the amplitude of the one or more transient DC voltages or potentials or potential or voltage waveforms which is preferably applied to the electrodes of the ion mobility spectrometer or separator 3 is preferably increased so that ions are no longer able to slip over the crest of the one or more potential hills as they are translated along the length of the ion mobility spectrometer or separator 3. Additionally or alternatively the velocity or rate at which the one or more transient DC potentials or voltages or DC potential or voltage waveforms are applied to the electrodes of the ion mobility spectrometer or separator 3 may be reduced.

In an embodiment the ion mobility spectrometer or separator 3 may be switched between a mode of operation wherein ions are separated according to their ion mobility and a mode of operation wherein ions are not substantially separated according to their ion mobility. This may be achieved by a combination of switching the gas pressure and/or altering the amplitude of the one or more transient DC voltages or potentials applied to the electrodes and/or by altering the velocity or rate at which the one or more transient DC voltages or potentials are applied to the electrodes of the ion mobility spectrometer or separator 3.

Figure 5:
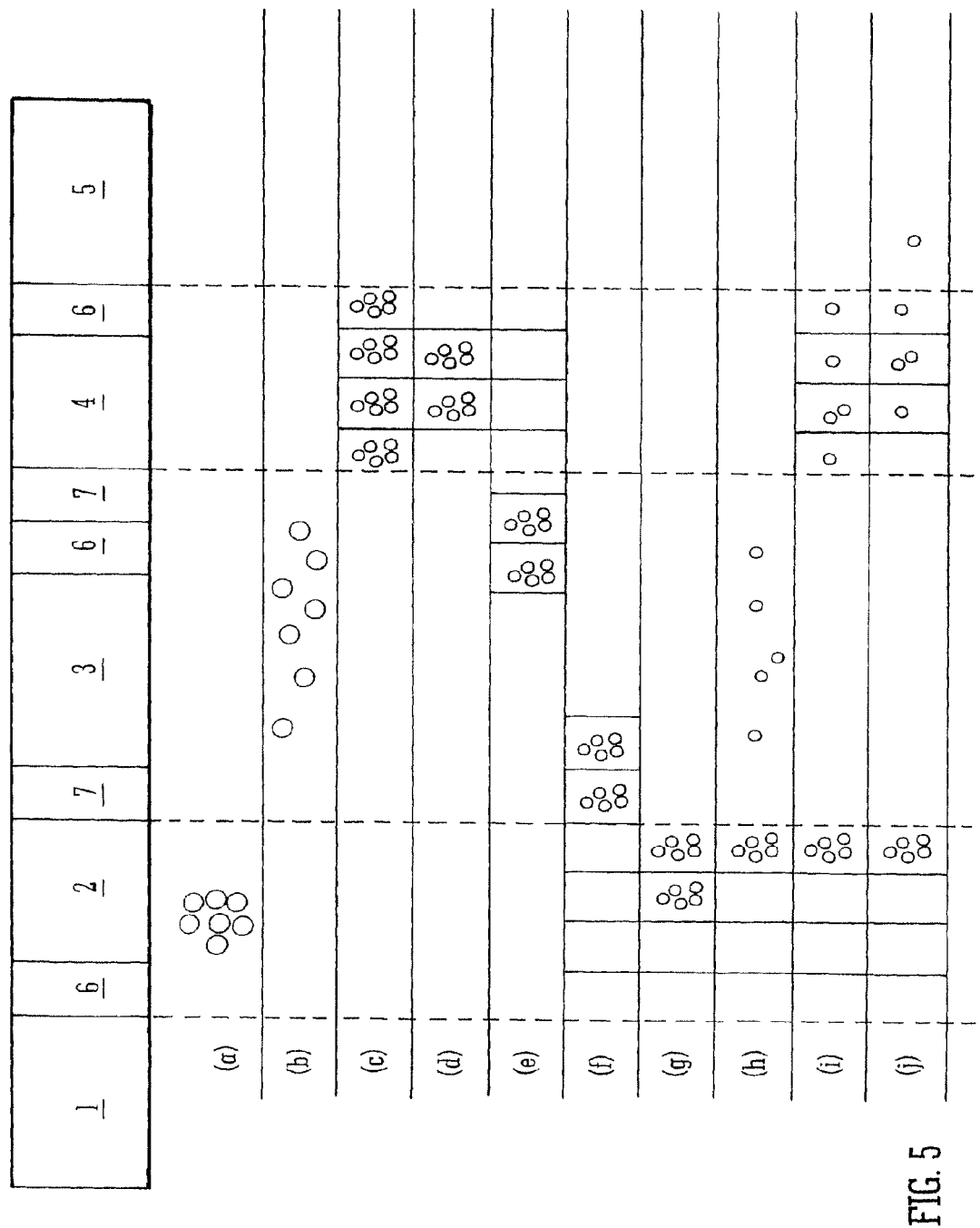
FIG. 5 illustrates a preferred mode of operation wherein parent or precursor ions are separated according to their ion mobility and are then fragmented upon entering a second downstream ion trap, and wherein selected groups of resulting fragment or daughter ions are passed upstream through the ion mobility spectrometer or separator to be trapped in a first ion trap, whereupon the fragment or daughter ions are then passed downstream through the ion mobility spectrometer or separator and are separated according to their ion mobility.

FIG. 5 illustrates a mode of operation wherein ions travel back and forth through the ion mobility spectrometer or separator 3 and wherein ions are also fragmented. Ions are preferably separated according to their ion mobility during some passes through the ion mobility spectrometer or separator 3 but are preferably not separated according to their ion mobility during other passes through the ion mobility spectrometer or separator 3.

The particular mode of operation shown in FIG. 5 will now be described in more detail. As shown in step (a) of FIG. 5, parent or precursor ions are preferably held initially within the first ion trap or ion guide 2. The parent or precursor ions are then preferably released from the first ion trap or ion guide 2 and preferably pass to the ion mobility spectrometer or separator 3. The parent or precursor ions are then preferably separated according to their ion mobility as the parent or precursor ions pass downstream through the ion mobility spectrometer or separator 3 as shown in step (b). The parent or precursor ions are then preferably accelerated as they reach the exit of the ion mobility spectrometer or separator 3 out from the ion mobility spectrometer or separator 3 and into the second ion trap or ion guide 4 such that the parent or precursor ions are preferably caused to fragment into first generation fragment ions upon entering the second ion trap or ion guide 4. The resulting first generation fragment, daughter, product or adduct ions are then preferably collected and isolated in a plurality of separate real axial potential wells which are preferably created within the second ion trap or ion guide 4 as shown in step (c). According to an embodiment all the first generation fragment ions resulting from the fragmentation of a particular parent or precursor ion are preferably trapped within the same real axial potential well within the second ion guide or ion trap 4. Fragment or daughter ions resulting from the fragmentation of other parent or precursor ions which subsequently emerge from the ion mobility spectrometer or separator 3 are preferably trapped in separate or different real axial potential wells created within the second ion guide or ion trap 4.

Once all the parent or precursor ions emerging from the ion mobility spectrometer or separator 3 have been fragmented upon entering the second ion guide or ion trap 4 and the resulting fragment or daughter ions have been trapped in separate real axial potential wells which are preferably translated downstream along the length of the second ion trap or ion guide 4, the real axial potential wells containing the separate packets of fragment ions within the second ion trap or ion guide 4 are preferably held stationary. Ions within one or more of the real axial potential wells may then be discarded as shown in step (d). The axial potential wells comprising the remaining packets of fragment ions are then preferably translated in an upstream direction along the length of the second ion trap or ion guide 4. The packets of ions are then preferably released from the second ion guide or ion trap 4 as a series of packets of ions. The packets of ions are then preferably transported in an upstream direction through the ion mobility spectrometer or separator 3 as shown in steps (e) and (f) towards the first ion trap or ion guide 2. As the fragment ions are transmitted back through the ion mobility spectrometer or separator 3 the fragment ions are preferably not separated according to their ion mobility as they pass upstream through the ion mobility spectrometer or separator 3. Instead, the ion mobility spectrometer or separator 3 is preferably operated in an ion guiding only mode of operation. Each packet of fragment ions is preferably trapped in a separate real axial potential well which is preferably translated along the length of the ion mobility spectrometer or separator 3. The various separate packets of fragment ions are then preferably received by the first ion trap or ion guide 2 and the fragment ions are preferably retained or isolated in separate real axial potential wells which are preferably formed or created within the first ion trap or ion guide 2 as shown in step (g).

The real axial potential wells or trapping regions provided in the first ion trap or ion guide 2 are then preferably moved or translated back downstream such that a first packet of fragment ions in a first axial potential well in the first ion trap or ion guide 2 is preferably released back into or towards the ion mobility spectrometer or separator 3. The first packet of fragment, daughter, product or adduct ions is then preferably separated according to their ion mobility as the fragment or daughter ions pass downstream through the ion mobility spectrometer or separator 3 towards the second ion trap or ion guide 4 as shown in step (h).

The fragment, daughter, product or adduct ions are preferably separated according to their ion mobility and preferably exit the ion mobility spectrometer or separator 3 and enter the second ion trap or ion guide 4. The ions are then preferably escorted or pass through the second ion trap or ion guide 4 and preferably pass to the mass analyser 5 for subsequent mass analysis. A second packet of fragment, daughter, product or adduct ions is then preferably released from the first ion trap or ion guide 2 into the ion mobility spectrometer or separator 3. The second packet of fragment, daughter, product or adduct ions is then preferably separated according to their ion mobility as the fragment or daughter ions pass downstream through the ion mobility spectrometer or separator 3 towards the second ion trap or ion guide 4. The fragment, daughter, product or adduct ions are then preferably received by the second ion trap or ion guide 4 and are preferably onwardly transmitted to the mass analyser 5.

Figure 6:
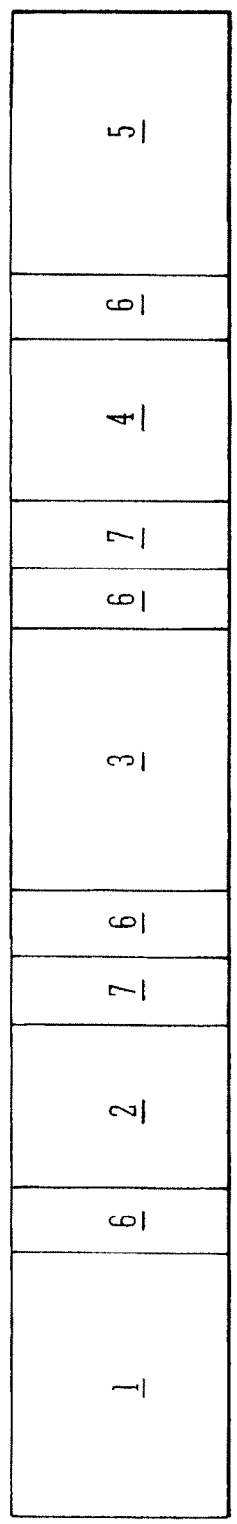
FIG. 6 shows a further embodiment of the present invention wherein the first ion trap, the ion mobility spectrometer or separator and the second ion trap are each provided in separate vacuum chambers.

FIG. 6 shows a similar embodiment to that shown in FIG. 4 except that an additional stage of differential pumping 6 is preferably provided between the first ion trap or ion guide 2 and the ion mobility spectrometer or separator 3. This allows the first ion trap or ion guide 2 to be maintained at a relatively lower pressure than that of the ion mobility spectrometer or separator 3. The ion mobility spectrometer or separator 3 may, for example, be maintained at a pressure in the range 0.1 mbar to 10 mbar whereas the first ion trap or ion guide 2 may preferably be maintained at a relatively lower pressure in the range of 0.001 to 0.1 mbar. Similarly, the second ion trap or ion guide 4 may also be maintained at a pressure in the range of 0.001 to 0.1 mbar which is also preferably lower than the pressure at which the ion mobility spectrometer or separator 3 is maintained. This preferably allows the first ion trap or ion guide 2 to be used more effectively to fragment ions by Collision Induced Decomposition than if the first ion trap or ion guide 2 were maintained at the same pressure as that of the ion mobility spectrometer or separator 3. Accordingly, ions may be induced to fragment in either the first ion trap or ion guide 2 and/or the second ion trap or ion guide 4.

Figure 7:
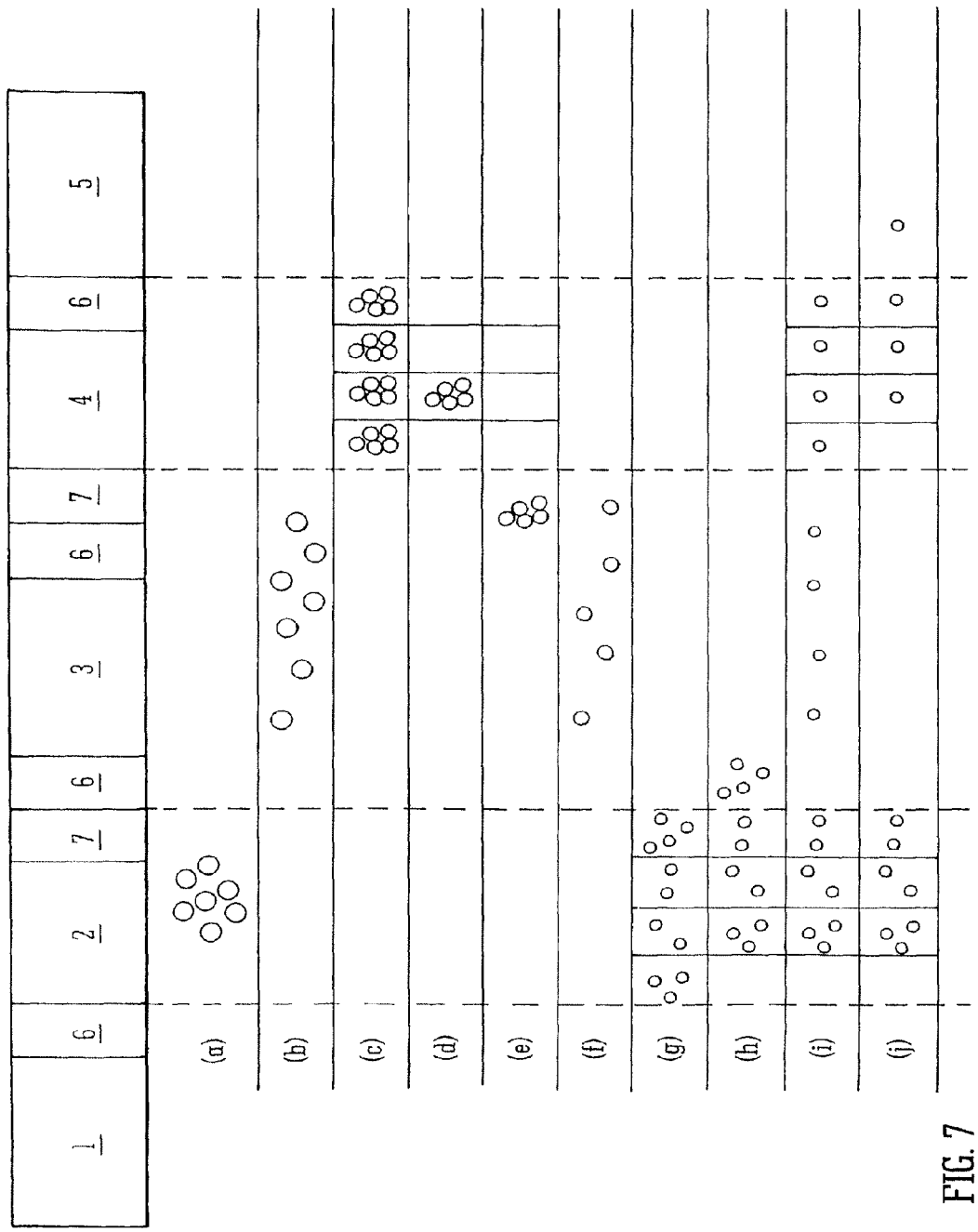
FIG. 7 illustrates a preferred mode of operation wherein parent or precursor ions are separated according to their ion mobility and are then fragmented into first generation fragment ions upon entering a second downstream ion trap, and wherein a selected group of first generation fragment ions is passed upstream through the ion mobility spectrometer or separator whereupon the first generation fragment ions are separated according to their ion mobility and wherein the first generation fragment ions are then fragmented into second generation fragment ions upon entering a first upstream ion trap.

FIG. 7 illustrates a mode of operation wherein ions are preferably fragmented in the first ion trap or ion guide 2 in addition to being fragmented in the second ion trap or ion guide 4. According to this embodiment parent or precursor ions are preferably released from the first ion trap or ion guide 2 and preferably pass into the ion mobility spectrometer or separator 3 as shown in step (a). The parent and precursor ions are then preferably separated according to their ion mobility as the parent or precursor ions pass downstream through the ion mobility spectrometer or separator 3 as shown in step (b). The parent or precursor ions exiting the ion mobility spectrometer or separator 3 are then preferably accelerated out of the ion mobility spectrometer or separator into the second ion trap or ion guide 4. This preferably causes the parent or precursor ions to fragment into first generation fragment ions upon entering the second ion trap or ion guide 4. Separate groups of first generation fragment ions are preferably collected and kept isolated in separate real axial potential wells which are preferably formed within the second ion trap or ion guide 4. The various groups of first generation fragment ions are preferably kept isolated from one another and the DC voltages or potentials which are preferably applied to the electrodes of the second ion trap or ion guide 4 are preferably held stationary so that the axial potential wells within the second ion trap or ion guide 4 are no longer translated downstream towards the mass analyser 5. One or more groups of first generation fragment ions trapped within the real axial potential wells formed or created within the second ion trap or ion guide 4 may then be discarded as shown in step (d). A first group of first generation fragment, daughter, product or adduct ions is then preferably released back into the ion mobility spectrometer or separator 3 as shown in step (e).

The first group of first generation fragment, daughter, product or adduct ions is then preferably separated according to their ion mobility as the first generation fragment, daughter, product or adduct ions pass upstream back through the ion mobility spectrometer or separator 3. The first generation fragment, daughter, product or adduct ions are then preferably accelerated out from the ion mobility spectrometer or separator 3 and into the first ion trap or ion guide 2. This preferably causes the first generation fragment, daughter, product or adduct ions to be further fragmented into second generation fragment, daughter, product or adduct ions. The second generation fragment, daughter, product or adduct ions are preferably collected and stored in separate real axial potential wells formed within the first ion trap or ion guide 2. The second generation fragment or daughter ions resulting from the fragmentation of each first generation fragment or daughter ions are preferably trapped or isolated in separate real axial potential wells created within the first ion trap or ion guide 2.

A first group of second generation fragment, daughter, product or adduct ions is then preferably released back into the ion mobility spectrometer or separator 3 as shown in step (h). The second generation fragment, daughter, product or adduct ions are then preferably separated according to their ion mobility as they pass downstream through the ion mobility spectrometer or separator 3 and are preferably received by the second ion trap or ion guide 4. The separated second generation fragment, daughter, product or adduct ions are then preferably escorted or translated through the second ion trap or ion guide 4 to the mass analyser 5 for subsequent mass analysis. Second and further packets of second generation fragment, daughter, product or adduct ions may then be released into the ion mobility spectrometer or separator 3 and may be separated according to their ion mobility.

It is clear that a mass spectrometer as illustrated, for example, in FIG. 6 wherein ions may pass through the ion mobility spectrometer or separator 3 in different directions either with or without being separated according to their ion mobility permits a large number of different permutations and combinations of sequences of operations to be carried out. Furthermore, ions may be induced to fragment upon exiting the ion mobility spectrometer or separator 3 at either the downstream and/or the upstream end of the ion mobility spectrometer or separator 3. As a result ions may be fragmented to a subsequent generation of fragment, daughter, product or adduct ions upon each passage of ions through the ion mobility spectrometer or separator 3 as and when required.

According to other less preferred embodiments ions may be fragmented by means other than by high energy collisions with gas molecules. For example, fragmentation techniques such as photo-dissociation, Electron Capture Dissociation (ECD), Electron Transfer Dissociation (ETD) and Surface Induced Decomposition (SID) may be used in order to fragment ions.

According to another embodiment when ions leave the ion mobility spectrometer or separator 3 the ions may instead be only partially energised by collisions with gas molecules such that instead of causing ions to be fragmented, the internal energy of the ions is preferably raised causing the ions to unfold or partially unfold without fragmenting. The ions may therefore be caused to change shape, structure or conformation. This may be achieved by raising the kinetic energy of the ions leaving the ion mobility spectrometer or separator 3 to a level that promotes an increase in internal energy without inducing fragmentation. The resulting change in cross section and hence ion mobility may then be measured or determined by passing the ions through the ion mobility spectrometer or separator 3 and determining any change in the transit time of the ions through the ion mobility spectrometer or separator 3.

According to another less preferred embodiment a Field Asymmetric Ion Mobility Spectrometer or FAIMS device may be provided instead of or in addition to an ion mobility spectrometer or separator 3. The Field Asymmetric Ion Mobility Spectrometer device is preferably arranged to separate ions according to their rate of change of ion mobility with electric field strength.

Although the present invention has been described with reference to preferred embodiments, it will be understood by those skilled in the art that various changes in form and detail may be made without departing from the scope of the present invention as set forth in the accompanying claims.

The invention claimed is:

1. A mass spectrometer comprising:
   a first ion trap or ion guide comprising a plurality of electrodes;
      a device for separating ions according to their ion mobility or rate of change of ion mobility with electric field strength, said device being arranged downstream of said first ion trap or ion guide;
      first transient DC voltage means arranged and adapted to apply one or more transient DC voltages or one or more transient DC voltage waveforms to electrodes forming said device; and
      a second ion trap or ion guide comprising a plurality of electrodes arranged downstream of said device, wherein said second ion trap or ion guide is arranged and adapted to receive a beam or group of ions and to partition said beam or group of ions such that a plurality of separate packets of ions are confined in said second ion trap or ion guide at any particular time, wherein each packet of ions is separately confined in a separate axial potential well formed within said second ion trap or ion guide.

2. A mass spectrometer as claimed in claim 1, wherein said first ion trap or ion guide is arranged and adapted in a mode of operation to receive ions which emerge from said device and to pass or transmit at least some of said ions, or at least some fragment, daughter, product or adduct ions derived from said ions, from said first ion trap or ion guide to said device.

3. A mass spectrometer as claimed in claim 1, wherein said first ion trap or ion guide is arranged and adapted to receive a beam or group of ions and to convert or partition said beam or group of ions such that a plurality or at least 1, 2, 3, 4, 5, 6, 7, 8, 9, 10, 11, 12, 13, 14, 15, 16, 17, 18, 19 or 20 separate packets of ions are confined or isolated in said first ion trap or ion guide at any particular time, and wherein each packet of ions is separately confined or isolated in a separate axial potential well formed within said first ion trap or ion guide.

4. A mass spectrometer as claimed in claim 1, further comprising:
   (i) first acceleration means arranged and adapted to accelerate ions into said first ion trap or ion guide wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of said ions are caused to fragment or react upon entering said first ion trap or ion guide; or
   (ii) second acceleration means arranged and adapted to accelerate ions into said second ion trap or ion guide wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of said ions are caused to fragment or react upon entering said second ion trap or ion guide.

5. A mass spectrometer as claimed in claim 1, further comprising a control system arranged and adapted to switch or repeatedly switch the potential difference through which ions pass prior to entering said first ion trap or ion guide or said second ion trap or ion guide between a relatively high fragmentation or reaction mode of operation wherein ions are substantially fragmented or reacted upon entering said second ion trap or ion guide and a relatively low fragmentation or reaction mode of operation wherein substantially fewer ions are fragmented or reacted or wherein substantially no ions are fragmented or reacted upon entering said second ion trap or ion guide.

6. A mass spectrometer as claimed in claim 1, further comprising
   (a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation On Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ("AP-MALDI") ion source; and (xviii) a Thermospray ion source; or
   (b) a collision, fragmentation or reaction device selected from the group consisting of: (i) a collision, fragmentation or reaction device arranged and adapted to fragment ions by Collision Induced Dissociation ("CID"); (ii) a Surface Induced Dissociation ("SID") fragmentation device; (iii) an Electron Transfer Dissociation fragmentation device; (iv) an Electron Capture Dissociation fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; and (xxviii) an ion-metastable atom reaction device for reacting ions to form adduct or product ions; or (c) mass analyser is selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; (xiv) an axial acceleration Time of Flight mass analyser; and (xv) a quadrupole rod set mass filter or mass analyser.

7. A mass spectrometer as claimed in claim 1, further comprising a mass filter or mass analyser, wherein said mass filter or mass analyser is selected from the group consisting of: (i) a quadrupole rod set mass filter or mass analyser; (ii) a Time of Flight mass filter or mass analyser; (iii) a Wein filter; and (iv) a magnetic sector mass filter or mass analyser; and wherein in a mode of operation:
(i) said mass filter or mass analyser is operated in a substantially non-resolving or ion guiding mode of operation; or
(ii) said mass filter or mass analyser is scanned or a mass to charge ratio transmission window of said mass filter or mass analyser is varied with time.

8. A mass spectrometer as claimed in claim 1, wherein in a mode of operation a first mass filter or mass analyser or a second mass filter or mass analyser is scanned or a mass to charge ratio transmission window of said first mass filter or mass analyser or said second mass filter or mass analyser is varied with time in synchronism with the operation of said device or the ion mobility or rate of change of ion mobility with electric field strength of ions emerging from or being transmitted to said device.

9. A mass spectrometer as claimed in claim 1, further comprising an ion gate or deflection system arranged upstream or downstream of said device.

10. A mass spectrometer as claimed in claim 1, wherein said device comprises:
(i) a drift tube comprising one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of said drift tube;
(ii) a multipole rod set or a segmented multipole rod set comprising a quadrupole rod set, a hexapole rod set, an octapole rod set or a rod set comprising more than eight rods;
(iii) an ion tunnel or ion funnel comprising a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of said electrodes have apertures which are of substantially the same size or area or which have apertures which become progressively larger or smaller in size or in area;
(iv) a stack or array of planar, plate or mesh electrodes, wherein said stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of said planar, plate or mesh electrodes are arranged generally in the plane in which ions travel in use; and
(v) a plurality of groups of electrodes arranged axially along the length of the ion trap or ion guide, wherein each group of electrodes comprises: (a) a first and a second electrode and means for applying a DC voltage to said first and second electrodes in order to confine ions in a first radial direction within said device; and (b) a third and a fourth electrode and means for applying an RF voltage to said third and fourth electrodes in order to confine ions in a second radial direction within said device.

11. A mass spectrometer as claimed in claim 1, wherein said device further comprises an RF voltage means arranged and adapted to apply an RF voltage to at least 5%, 10%, 15%, 20%, 25%, 30%, 35%, 40%, 45%, 50%, 55%, 60%, 65%, 70%, 75%, 80%, 85%, 90%, 95% or 100% to a plurality of electrodes forming said device in order to confine ions radially within said device.

12. A mass spectrometer as claimed in claim 1, wherein said first transient DC voltage means is arranged and adapted to urge at least some ions upstream or downstream along at least 5%, 10%, 15%, 20%, 25%, 30%, 35%, 40%, 45%, 50%, 55%, 60%, 65%, 70%, 75%, 80%, 85%, 90%, 95% or 100% of the axial length of said device.

13. A mass spectrometer as claimed in claim 1, wherein said second ion trap or ion guide is arranged in a mode of operation to pass or transmit ions from said second ion trap or ion guide to said first ion trap or ion guide.

14. A mass spectrometer as claimed in claim 13, wherein said second ion trap or ion guide is arranged in a mode of operation to pass or transmit ions from said second ion trap or ion guide to first ion trap or ion guide multiple times before transporting said ions to a mass analyser for subsequent mass analysis.

15. A method of mass spectrometry comprising:
providing a first ion trap or ion guide;

separating ions according to their ion mobility or rate of change of ion mobility with electric field strength in a device, said device being arranged downstream of said first ion trap or ion guide;

applying one or more transient DC voltages or one or more transient DC voltage waveforms to electrodes forming said device;

providing a second ion trap or ion guide arranged downstream of said device;

receiving a beam or group of ions in said second ion trap or ion guide and partitioning said beam or group of ions such that a plurality of separate packets of ions are confined in said second ion trap or ion guide at any particular time, wherein each packet of ions is separately confined in a separate axial potential well formed within said second ion trap or ion guide.

16. A method of mass spectrometry comprising:

providing a first ion trap or ion guide;

providing a device for separating ions according to their ion mobility or rate of change of ion mobility with electric field strength, said device being arranged downstream of said first ion trap or ion guide;

providing a second ion trap or ion guide arranged downstream of said first ion trap or guide; and passing ions from said first ion trap or ion guide to said device and onwards to said second ion trap or ion guide; and then passing at least some of said ions or at least some fragment, daughter, product or adduct ions derived from said ions from said second ion trap or ion guide onwards to said first ion trap or ion guide.

17. A method as claimed in claim 16, comprising forming a plurality of axial potential wells within said second ion trap or ion guide and partitioning multiple ions present in said second ion trap or ion guide at the same time into a plurality of separate packets of ions wherein each packet of ions is separately confined in a separate axial potential well of said axial potential wells.

18. A method as claimed in claim 16, comprising repeating the steps of passing ions from said first ion trap or ion guide to said device and onwards to said second ion trap or ion guide and then passing at least some of said ions or at least some fragment, daughter, product or adduct ions derived from said ions from said second ion trap or ion guide to said first ion trap or ion guide multiple times.

19. A method as claimed in claim 18, comprising varying the number of passes of ions through said device.

20. A method as claimed in claim 18, comprising, at the end of each cycle of operation, transporting ions from said second ion trap or ion guide to a mass analyser for subsequent mass analysis.

21. A mass spectrometer comprising:

a first ion trap or ion guide;

a device for separating ions according to their ion mobility or rate of change of ion mobility with electric field strength, said device being arranged downstream of said first ion trap or ion guide; and a second ion trap or ion guide arranged downstream of said first ion trap or guide wherein said first ion trap or ion guide is arranged to pass or transmit ions to said device and onwards to said second ion trap or ion guide, and wherein said second ion trap or ion guide is arranged to pass at least some of said ions or at least some fragment, daughter, product or adduct ions derived from said ions onwards to said first ion trap or ion guide.

* * * * *